United States Patent [19]
Armentano et al.

[11] Patent Number: 5,981,275
[45] Date of Patent: Nov. 9, 1999

[54] TRANSGENE EXPRESSION SYSTEM FOR INCREASED PERSISTENCE

[75] Inventors: Donna Armentano, Belmont; John Marshall, Hopedale; Nelson S. Yew, West Upton; Seng H. Cheng, Wellesley; Richard J. Gregory, Westford, all of Mass.

[73] Assignee: Genzyme Corporation, Cambridge, Mass.

[21] Appl. No.: 08/839,552

[22] Filed: Apr. 14, 1997

[51] Int. Cl.⁶ ................................................ C12N 15/00
[52] U.S. Cl. ........................................................ 435/320.1
[58] Field of Search ............................ 435/172.3, 320.1; 514/44

[56] References Cited

U.S. PATENT DOCUMENTS

| | | | |
|---|---|---|---|
| 5,283,185 | 2/1994 | Epand et al. | 435/172.3 |
| 5,635,380 | 6/1997 | Naftilan et al. | 435/172.3 |
| 5,719,131 | 2/1998 | Harris et al. | 514/44 |

FOREIGN PATENT DOCUMENTS

| | | |
|---|---|---|
| WO9428938 | 12/1994 | WIPO . |
| WO9613596 | 5/1996 | WIPO . |
| WO9618372 | 6/1996 | WIPO . |
| WO9630534 | 10/1996 | WIPO . |
| WO9708298 | 3/1997 | WIPO . |

OTHER PUBLICATIONS

Verma et al. Gene therapy—Promises, Problems, and Prospects. Nature, vol. 389, pp. 239–242, Sep. 18, 1997.
Wagner et al. Toward Cystic Fibrosis Gene Therapy. Annual Reviews in Medicine, vol. 48, pp. 203–216, 1997.
Sandhu et al. Human Gene Therpy. Critical Reviews in Biotechnology, vol. 17, No. 4, pp. 307–326, 1997.
Bridge et al., Adenovirus early region 4 and viral DNA synthesis, Virology 193: 794–80, 1993.
Berkner, K.L., Curr. Top. Micro. Immunol. 158:39–66, 1992.
Graham, F.L., J. Gen. Virol. 36:59–72, 1977.
Zhou et al., J. Virol. 70:7030–7038, 1996.
Krougliak et al., Hum. Gene Ther. 6:1575–1586, 1995.
Wang et al., Gene Ther. 2:775–783, 1995.
Caravokyri et al., J. Virol. 69:6627–6633, 1995.
Kochanek et al., Proc. Natl. Acad. Sci. USA 93:5731–5736, 1996.
Fisher et al., Virology 217:11–22, 1996.
Wills et al., Human Gene Therapy 5:1079–188, 1994.
Vincent et al., Nature Genetics 5:130–134, 1993.
Descamps et al., Human Gene Therapy 5:979–985, 1994.
Stratford–Perricaudet et al., Human Gene Therapy 1:241–256, 1990.
Ye et al., J. Biol. Chem. 271;3639–3646, 1996.
Mitani et al., Human Gene Therapy 5:941–948, 1994.
Haddada et al., Human Gene Therapy 4:703–711, 1993.
Jaffe et al., Nature Genetics 1:372–378, 1992.
Ohwada et al., Blood 88:778–784, 1996.
Ohwada et al., Hum. Gene Ther. 7:1567–1576, 1996.
Zabner et al., Nature Genetics 6:75–83, 1994.
Rich et al., Human Gene Therapy 4:461–476, 1993.
Zabner et al., Cell 75:207–216, 1993.
Crystal et al., Nature Genetics 8:42–51, 1994.
Zabner et al., J. Clin. Invest. 97:1504–1511, 1996.
Yang et al., J. Virol. 69:2004–2015, 1995.
Yang et al., Proc. Natl. Acad. Sci. USA 91:4407–4411, 1994.
Zsengeller et al., Hum Gene Ther. 6:457–467, 1995.
Worgall et al., Hum Gene Ther. 8:37–44, 1997.
Kaplan et al., Hum. Gene Ther. 8:45–56, 1997.
Crystal, R., Science 270:404–410, 1995.
Fang et al., Hum. Gene Ther. 6:1039–1044, 1995.
Kay et al., Nature Genetics 11:191–197, 1995.
Guo et al., Gene Therapy 3:802–801, 1996.
Tripathy et al., Nature Med. 2:545–550, 1996.
Yang et al., Nature Genetics 7:362–369, 1994.
Lieber et al., J. Virol. 70:8944–8960, 1996.
Gorziglia et al., J. Virol. 70:4173–4178.
Wold et al., Trends Microbiol. 437–443, 1994.
Boshart et al., Cell 41:521–530, 1985.
Yew et al., Hum. Gene Ther. 8:575–584, 1997.
Armentano et al., Hum. Gene Ther. 6:1343–1353, 1995.
Felgner et al., Proc. Natl. Acad. Sci. USA 84:7413–7417, 1987.
Behr et al., Proc. Natl. Acad. Sci. USA 86:6982–6986, 1989.
Felgner et al., J. Biol. Chem. 269:2550–2561, 1994.
Kalderon et al., Cell 39:499–509, 1984.
Liebowitz et al., Curr. Top. Micro. Immunol. 87:43–172, 1979.
Hehir et al., J. Virol. 70:8459–8467, 1996.
Halbert et al., J. Virol. 56:250–257, 1985.

*Primary Examiner*—Brian R. Stanton
*Assistant Examiner*—Deborah J. R. Clark
*Attorney, Agent, or Firm*—Baker & Botts, L.L.P.

[57] ABSTRACT

The invention is directed to a transgene expression system comprising a transcription unit which contains a transgene operably linked to expression control sequences, preferably the CMV promoter, and which is delivered simultaneously with all or part of the adenovirus E4 genomic region to a cell in order to facilitate persistent expression of the transgene. The components of the transgene expression system can be delivered by vectors including plasmids and/or viruses and may be complexed with cationic amphiphiles to facilitate entry into a cell. The invention is also directed to methods for the production of the transgene expression system. The invention is further directed to compositions that contain the transgene expression system and to methods for the use of such compositions to deliver transgenes encoding biologically active proteins to cells.

4 Claims, 11 Drawing Sheets

TRANSGENE EXPRESSION SYSTEM FOR INCREASED PERSISTENCE

INTRODUCTION

The invention is directed to a transgene expression system which contains a transcription unit containing a transgene operably linked to expression control sequences, preferably the cytomegalovirus immediate early promoter, and which is delivered concurrently with all or part of the adenovirus E4 genomic region to a cell in order to facilitate persistent expression of the transgene in the cell. The components of the transgene expression system can be delivered by one or more vectors, including plasmids and/or viruses and may be complexed with cationic amphiphiles to facilitate entry into a cell. The invention is also directed to methods for the production of the transgene expression system. The invention is further directed to compositions containing the transgene expression system and to methods for the use of such compositions to deliver transgenes encoding biologically active proteins to cells in vivo and obtain persistent expression thereof.

BACKGROUND OF THE INVENTION

Adenovirus is a non-enveloped, nuclear DNA virus with a genome of about 36 kb, which has been well-characterized through studies in classical genetics and molecular biology (Horwitz, M. S., "Adenoviridae and Their Replication," in *Virology*, 2nd edition, Fields et al., eds., Raven Press, New York, 1990). The viral genes are classified into early (known as E1–E4) and late (known as L1–L5) transcriptional units, referring to the generation of two temporal classes of viral proteins. The demarcation between these events is viral DNA replication.

Recombinant adenoviruses have several advantages for use as gene transfer vectors, including tropism for both dividing and non-dividing cells, minimal pathogenic potential, ability to replicate to high titer for preparation of vector stocks, and the potential to carry large inserts (Berkner, K. L., Curr. Top. Micro. Imnmunol. 158:39–66, 1992; Jolly, D., Cancer Gene Therapy 1:51–64, 1994).

The cloning capacity of an adenovirus vector is proportional to the size of the adenovirus genome present in the vector. For example, a cloning capacity of about 8 kb can be created from the deletion of certain regions of the virus genome dispensable for virus growth, e.g., E3, and the deletion of a genomic region such as E1 whose function may be restored in trans from 293 cells (Graham, F. L., J. Gen. Virol. 36:59–72, 1977) or A549 cells (Imler et al., Gene Therapy 3:75–84, 1996). Such E1-deleted vectors are rendered replication-defective. The upper limit of vector DNA capacity for optimal carrying capacity is about 105%–108% of the length of the wild-type genome. Further adenovirus genomnic modifications are possible in vector design using cell lines which supply other viral gene products in trans, e.g., complementation of E2a (Zhou et al., J. Virol. 70:7030–7038, 1996), complementation of E4 (Krougliak et al., Hum. Gene Ther. 6:1575–1586, 1995; Wang et al., Gene Ther. 2:775–783, 1995), or complementation of protein IX (Caravokyri et al., J. Virol. 69:6627–6633, 1995; Krougliak et al., Hum. Gene Ther. 6:1575–1586, 1995). Maximal carying capacity can be achieved using adenoviral vectors deleted for all viral coding sequences (Kochanek et al., Proc. Natl. Acad. Sci. USA 93:5731–5736, 1996; Fisher et al., Virology 217:11–22, 1996).

Transgenes that have been expressed to date by adenoviral vectors include p53 (Wills et al., Human Gene Therapy 5:1079–188, 1994); dystrophin (Vincent et al., Nature Genetics 5:130–134, 1993; erythropoietin (Descamps et al., Human Gene Therapy 5:979–985, 1994; ornithine transcarbamylase (Stratford-Perricaudet et al., Human Gene Therapy 1:241–256, 1990; We et al., J. Biol. Chem. 271;3639–3646, 1996;); adenosine deaminase (Mitani et al., Human Gene Therapy 5:941–948, 1994); interleukin-2 (Haddada et al., Human Gene Therapy 4:703–711, 1993); and α1-antitrypsin (Jaffe et al., Nature Genetics 1:372–378, 1992); thrombopoietin (Ohwada et al., Blood 88:778–784, 1996); and cytosine deaminase (Ohwada et al., Hum. Gene Ther. 7:1567–1576, 1996).

The particular tropism of adenoviruses for cells of the respiratory tract has particular relevance to the use of adenovirus in gene therapy for cystic fibrosis (CF), which is the most common autosomal recessive disease in Caucasians. Mutations in the cystic fibrosis transmembrane conductance regulator (CFTR) gene that disturb the cAMP-regulated $Cl^-$ channel in airway epithelia result in pulmonary dysfinction (Zabner et al., Nature Genetics 6:75–83, 1994). Adenovirus vectors engineered to carry the CFTR gene have been developed (Rich et al., Human Gene Therapy 4:461–476, 1993) and studies have shown the ability of these vectors to deliver CFTR to nasal epithelia of CF patients (Zabner et al., Cell 75:207–216, 1993), the airway epithelia of cotton rats and primates (Zabner et al., Nature Genetics 6:75–83, 1994), and the respiratory epithelium of CF patients (Crystal et al., Nature Genetics 8:42–51, 1994). Recent studies have shown that administering an adenoviral vector containing a DNA sequence encoding CFTR to airway epithelial cells of CF patients can restore a functioning chloride ion channel in the treated epithelial cells (Zabner et al., J. Clin. Invest. 97:1504–1511, 1996; allowed U.S. patent application Ser. No. 08/136,742, filed Oct. 13, 1993).

The use of adenovirus vectors in gene transfer studies to date indicates that persistence of transgene expression is often transient. At least some of the limitation is due to the generation of a cellular immune response to the viral proteins which are expressed antigentically even from a replication-defective vector, triggering a pathological inflammatory response which may destroy or adversely affect the adenovirus-infected cells (Yang et al., J. Virol. 69:2004–2015, 1995; Yang et al., Proc. Natl. Acad. Sci. USA 91:4407–4411, 1994; Zsengeller et al., Hum Gene Ther. 6:457–467, 1995; Worgall et al., Hum. Gene Ther. 8:37–44, 1997; Kaplan et al., Hum. Gene Ther. 8:45–56, 1997). Because adenovirus does not integrate into the cell genome, host immune responses that destroy virions or infected cells have the potential to limit adenovirus-based gene therapy. An adverse immune response poses a serious obstacle for high dose administration of an adenovirus vector or for repeated administration (Crystal, R., Science 270:404–410, 1995).

In order to circumvent the host immune response which limits the persistence of transgene expression, various strategies have been employed, generally involving either the modulation of the immune response itself or the engineering of a vector that decreases the immune response. The administration of immunosuppressive agents together with vector administration has been shown to prolong transgene persistence (Fang et al., Hum. Gene Ther. 6:1039–1044, 1995; Kay et al., Nature Genetics 11:191–197, 1995; Zsellenger et al., Hum. Gene Ther. 6:457–467, 1995).

The lack of persistence in the expression of adenovirus vector-delivered transgenes may also be due to limitations imposed by the choice of promoter or transgene contained in the transcription unit (Guo et al., Gene Therapy 3:802–801, 1996; Tripathy et al., Nature Med. 2:545–550, 1996).

Modifications to genomic adenoviral sequences contained in the recombinant vector have been attempted in order to decrease the host immune response (Yang et al., Nature Genetics 7:362–369, 1994; Lieber et al., J. Virol. 70:8944–8960, 1996; Gorziglia et al., J. Virol. 70:4173–4178; Kochanek et al., Proc. Natl. Acad. Sci. USA 93:5731–5736, 1996; Fisher et al., Virology 217:11–22, 1996). The adenovirus E3 gp19K protein can complex with MHC Class I antigens and retain them in the endoplasmic reticulum, which prevents cell surface presentation and killing of infected cells by cytotoxic T-lymphocytes (CTLs) (Wold et al., Trends Microbiol. 437–443, 1994), suggesting that its presence in a recombinant adenoviral vector may be beneficial.

Experiments in which adenovirus vectors were introduced into nude mice demonstrated that the context of the adenovirus E4 genomic region was a determinant in the persistence of expression, especially when the CMV promoter was used to control expression of the transgene (Kaplan et al., Hum. Gene Ther. 8:45–56, 1997; Armentano et al., J. Virol. 71:2408–2416, 1997).

Therefore, the current state of adenoviral vector-based gene delivery requires the development of transgene expression systems which demonstrate the capability for persistence and sustained expression of a transgene.

SUMMARY OF THE INVENTION

The invention is directed to a transgene expression system which contains a transcription unit containing a transgene operably linked to expression control sequences, preferably the cytomegalovirus immediate early promoter, and which is delivered concurrently with all or part of the adenovirus E4 genomic region to a cell in order to facilitate persistent expression of the transgene. The components of the transgene expression system can be delivered by one or more plasmids and/or viruses and may be complexed with cationic amphiphiles to facilitate entry into a cell. The invention is also directed to methods for the production of the transgene expression system. The invention is further directed to compositions that contain the transgene expression system and to methods for the use of such compositions to deliver transgenes to cells in vivo and obtain persistent expression thereof.

DETAILED DESCRIPTION OF THE INVENTION

Figure 1:
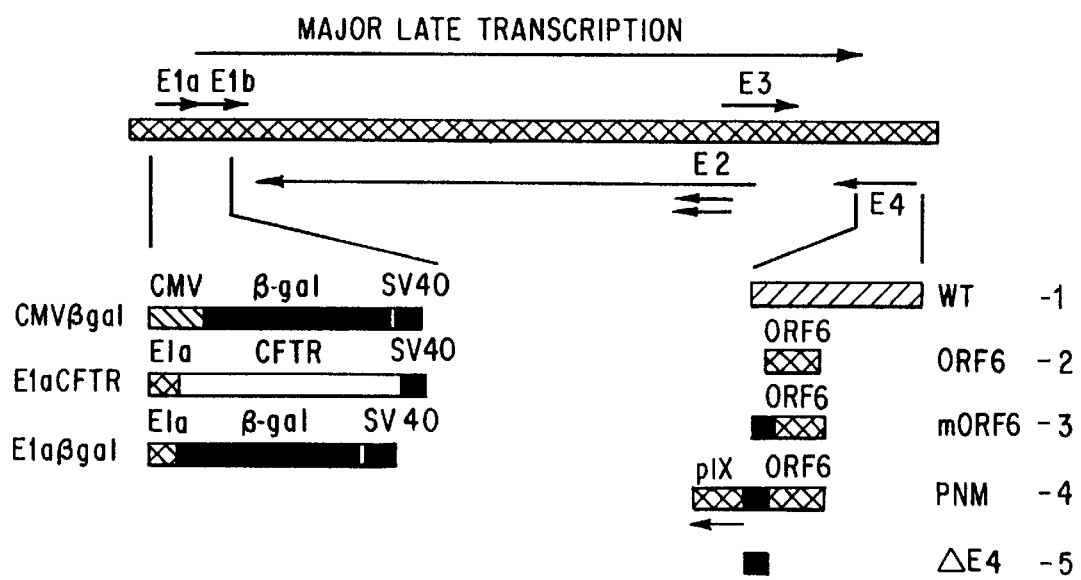
FIG. 1 shows a schematic diagram of the genomic structure of the CMVβgal, E1ACFTR and E1Aβgal adenoviral vector series.

The invention is directed to a transgene expression system which comprises DNA sequences encoding a transcription unit containing a transgene operably linked to expression control sequences, preferably the cytomegalovirus (CMV) immediate early promoter, and DNA sequences encoding all or part of the adenovirus E4 genomic region, which are simultaneously delivered to a cell in order to facilitate persistent expression of the transgene. These components of the transgene expression system can be delivered by one or more plasmids and/or viruses and may be complexed with cationic amphiphiles to facilitate entry into a cell. The invention is also directed to methods for the production of the transgene expression system. The invention is further directed to compositions that contain the transgene expression system and to methods for the use of such compositions to deliver transgenes to cells in vivo and obtain persistent expression thereof.

Transgene is defined herein as any gene that is not native to the adenovirus genome. Persistent expression is defined as generating a sustained level of expression of a transgene over time.

The invention is also directed to novel adenoviral vectors which are capable of providing for persistent expression of the transgene because the vector contains all components of the transgene expression system of the invention. The vector contains a transgene under the control of the CMV promoter. The adenovirus E4 region is preferably retained in the vector to increase the persistence of expression from the transgene under the control of the CMV promoter. The adenovirus genome of the vector may contain other modifications to the adenovirus genome e.g., is deleted for all or part of the E1 region and all or part of the E3 region.

The transcription unit of the transgene expression system of the invention is defined herein as the DNA sequences encoding a transgene, any expression control sequences such as a promoter or enhancer, a polyadenylation element, and any other regulatory elements that may be used to modulate or increase expression, all of which are operably linked in order to allow expression of the transgene. The use of any expression control sequences, or regulatory elements, which facilitate persistent expression of the transgene is within the scope of the invention. Such sequences or elements may be capable of generating tissue-specific expression or be susceptible to induction by exogenous agents or stimuli.

Preferably, the cytomegalovirus (CMV) immediate early promoter (Boshart et al., Cell 41:521–530, 1985) is used to control expression of the transgene in a transcription unit, or a truncated fragment of this promoter which functions analogously may be used. The CMV promoter is positioned 5' to the transgene in a transcription unit. Portions of the full-length promoter can be tested for their ability to allow persistent expression of a transgene using assays described below. Preferably, the region of the CMV promoter from nucleotides −523 to −14 or −522 to +72 may be used in the transgene expression system of the invention. A further preferred embodiment for use in the invention is a CMV promoter comprising nucleotides −522 to +72, with a deletion from −462 to −141.

Polyadenylation signals which may be positioned at the 3' end of the transgene in a transcription unit include, but are not limited to, those derived from bovine growth hormone (BGH) and SV40.

The use of an intron positioned into a transcription unit of the invention in order to activate the splicing apparatus and enhance message stability is within the scope of the invention. A preferred intron for such use is the hybrid intron described in Yew et al., Hum. Gene Ther. 8:575–584, 1997.

Transgenes which can be delivered and expressed from a transcription unit of the invention include, but are not limited to, those encoding enzymes, blood derivatives, hormones, lymphokines such as the interleukins and interferons, coagulants, growth factors, neurotransmitters, tumor suppressors, apolipoproteins, antigens, and antibodies, and other biologically active proteins. Specific transgenes which may be encoded by the transcription units of the invention include, but are not limited to, cystic fibrosis transmembrane regulator (CFTR), dystrophin, glucocerebrosidase, tumor necrosis factor, p53, retinoblastoma (Rb), and adenosine deaminase (ADA). Transgenes encoding antisense molecules or ribozymes are also within the scope of the invention.

A further component of the transgene expression system of the invention is all or part of the adenovirus E4 genomic region which is provided concurrently with the transcription unit to a cell in order to prevent transcriptional down-regulation of transgene expression and therefore facilitate increased persistence. The gene products of the E4 region may be provided in trans to maintain persistence since the E4 DNA sequence is not required in cis to the transcription unit in order to function. The E4 region contains several open reading frames (ORF), including ORFs 1, 2, 3, ¾, 6, and ⁶⁄₇. The adenovirus E4 genomic region may be provided as a full length sequence, or portions of the E4 region or individual open reading frames may be used which function analogously to the full-length sequence to promote persistent expression of the transgene contained in the transcription unit. Where individual open reading frames of the E4 region are used to prevent transcriptional down-regulation of the transgene, such genes may be placed under the control of the native E4 promoters, or, alternatively, may be placed under the control of heterologous promoters. In one embodiment of the invention, the E4 open reading frames may be placed under the control of a promoter that causes sufficient expression of the E4 open reading frame(s) so that sufficient protein product is available for the transcription unit, e.g., using the CMV promoter separately or a promoter of similar strength.

In a preferred embodiment of the invention, the adenovirus E4 sequences provided on a plasmid or adenoviral vector retain the coding sequences for the ORF3 gene in order to facilitate persistent expression.

The components of the transgene expression system of the present invention may be delivered to a cell on one or more vectors, which include, but are not limited to, plasmids and viruses. In a specific embodiment of the invention. one or more transcription units may be provided on a plasmid, where the CMV promoter is used to control expression and is positioned 5' to a transgene. As noted above, the adenovirus E4 component of the transgene expression system can be provided in cis or in trans to the transgene transcription unit. In a preferred embodiment of the invention, the adenovirus E4 region is provided in cis to the transgene transcription unit where the E4 region is engineered into the same vector, e.g., plasmid or virus, as the transcription unit. This particular embodiment is advantageous in that only one vehicle is required to deliver all DNA sequences required for persistent expression of the transgene. Alternatively, the E4 region may be provided in trans to the transcription unit on a separate vector that is co-delivered to a cell.

The components of the transgene expression system can be delivered to a cell using a hybrid vector delivery system in which some of the components are delivered by plasmid, and other components are delivered on a virus. Preferably, such a hybrid delivery system contains the transgene transcription unit on a plasmid, and contains the adenovirus E4 sequences in trans on a virus. In a preferred embodiment, the virus is an adenovirus. Delivery of the transgene expression system using this hybrid vector system also can utilize cationic molecule-based delivery, for example, to deliver both plasmid and virus, or, alternatively, may use cationic molecule-based delivery to deliver the plasmid to a cell and allow the virus to infect the cell simultaneously. In a preferred embodiment of the invention, both plasmid and virus are co-delivered by the same transfer route, e.g., cationic molecule-based delivery, in order to control the stoichiometry of the transgene expression system components.

Novel adenovirus vectors can be used to deliver the components of the transgene expression system and are within the scope of the invention. In this embodiment of the invention, an adenoviral vector is engineered to contain the transgene transcription unit, wherein the transgene is preferably under the control of the CMV promoter, as well as retaining all or part of the E4 genomic region. The virus is preferably a replication-defective adenoviral vector, which may contain all or part of the other genomic regions of the adenovirus genome, e.g., E1, E2 and E3, and in which the transgene transcription unit is preferably inserted into a deleted E1 region. In a preferred embodiment of the invention, such an adenoviral vector retains the coding sequences for the E4 ORF3 gene and E3 gp19K gene. Examples of vector backbones which can be used to contain a transcription unit and which include the adenovirus E4 region include Ad2/CFTR-1 (allowed U.S. patent application Ser. No. 08/136,742 filed Oct. 13, 1993; Rich et al., Human Gene Therapy 4:461–476, 1993, incorporated herein by reference). It is within the level of the skilled artisan to construct adenoviral vectors which contain a transcription unit of the invention engineered into such vectors.

To create the recombinant adenoviral vectors of the invention which contain a transcription unit, a plasmid containing the transcription unit inserted into an adenovirus genomic fragment is co-transfected with a linearized viral genome derived from an adenoviral vector of interest into a recipient cell under conditions whereby homologous recombination occurs between the genomic fragment and the virus. Preferably, the transcription unit is engineered into the site of an E1 deletion. As a result, the transcription unit encoding a desired transgene is inserted into the adenoviral genome at the site in which it was cloned into the plasmid, creating a recombinant adenoviral vector. Following the homologous recombination, the vector genome is encapsidated into virions as evidenced by the formation of viral plaques. Preparation of replication-defective vector stocks which contain the transcription unit and/or the adenovirus E4 region can be accomplished using cell lines that complement viral genes deleted from the vector, e.g., 293 or A549 cells containing the deleted adenovirus E1 genomic sequences. After amplification of plaques in suitable complementing cell lines, the viruses can be recovered by freeze-thawing and subsequently purified using cesium chloride centrifugation. Alternatively, virus purification can be performed using chromatographic techniques, e.g., as set forth in International Application No. PCT/US96/13872, filed Aug. 30, 1996, incorporated herein by reference.

Titers of replication-defective adenoviral vector stocks can be determiined by plaque formation in a complementing cell line, e.g., 293 cells. For example, end-point dilution using an antibody to the adenoviral hexon protein may be used to quantitate virus production (Armentano et al., Hum. Gene Ther. 6:1343–1353, 1995).

Plasmids which may be used to deliver the transgene transcription unit and/or the adenovirus E4 sequence include such vectors as pCMVβ (Clontech, Palo Alto, Calif.), in which a transgene can be placed under the control of the CMV promoter. The invention contemplates the use of any plasmids into which the components of the transgene expression system can be engineered using standard recombinant DNA technology and which facilitate the persistent expression of the transgene.

Other vectors, such as plasmids containing the transcription unit and/or the adenovirus E4 region of the transgene expression system can be constructed using standard techniques of recombinant DNA technology. Large scale production and purification can be performed using techniques well known to those skilled in the art (see, e.g., *Current Protocols in Molecular Biology*, Ausubel et al., eds., John Wiley & Sons, Inc., New York, 1995).

The DNA components of the transgene expression system are preferably contained on various vectors, including plasmids and/or viruses for delivery to a cell. However, the delivery of such components to a cell in the form of naked DNA is also within the scope of the invention, using such routes as transfection, electroporation, microinjection, and other DNA transfer methods. Such transfer may be facilitated by the use of cationic molecules, such as cationic lipids as disclosed in PCT Publication No. WO96/18372, published Jun. 20, 1996, incorporated herein by reference.

Where a marker or reporter gene is used as the transgene to determine the persistence of expression in the transgene expression system of the invention, a plasmid such as pCF1-CAT, containing the chloramphenicol acetyltransferase (CAT) gene under the control of the CMV promoter (described in Example 6, infra.), can be used. Other marker genes which can be used include, but are not limited to, the genes encoding β-galactosidase and luciferase.

The transgene expression system can be used to facilitate persistence by preventing down-regulation of transgene expression from expression control sequences. In a particular embodiment of the invention, the transgene expression system components can be used in any vector or gene delivery system, e.g., a retroviral vector containing a transgene operably linked to the CMV promoter and further containing all or part of the adenovirus E4 region.

Where any or all of the components of the transgene expression system are contained on one or more plasmids and/or viruses, the entry of such vehicles into a cell may be accomplished using mediated delivery, such as with the use of cationic amphiphiles, including lipids.

Cationic amphiphiles have a chemical structure which encompasses both polar and non-polar domains so that the molecule can simultaneously facilitate entry across a lipid membrane with its non-polar domain while its cationic polar domain attaches to a biologically useful molecule to be transported across the membrane.

Cationic amphiphiles which may be used to form complexes with the plasmids or viruses containing the transgene expression system of the invention include, but are not limited to, cationic lipids, such as DOTMA (Felgner et al., Proc. Natl. Acad. Sci. USA 84:7413–7417, 1987) (N-[1-(2, 3-dioletloxy)propyl]-N,N,N-trimethylammonium chloride); DOGS (dioctadecylamidoglycylspermine) (Behr et al., Proc. Natl. Acad. Sci. USA 86:6982–6986, 1989); DMRIE (1,2-dimyristyloxypropyl-3-dimethyl-hydroxyethyl ammonium bromide) (Felgner et al., J. Biol. Chem. 269:2550–2561, 1994; and DC-chol (3B [N-N', N'-dimethylaminoethane)-carbamoyl] cholesterol) (U.S. Pat. No. 5,283,185 to Epand et al.). The use of other cationic amphiphiles recognized in the art or which come to be discovered is within the scope of the invention.

In preferred embodiments of the invention, the cationic amphiphiles useful to complex with and facilitate transfer of the plasmids and/or viruses of the invention are those lipids which are described in PCT Publication No. WO96/18372, published Jun. 20, 1996, which is incorporated herein by reference. Preferred cationic amphiphiles described herein to be used in the delivery of the plasmids and/or viruses are GL-53, GL-67, GL-75, GL-87, GL-89, and GL-120, including protonated, partially protonated, and deprotonated forms thereof. Further embodiments include the use of non-T-shaped amphiphiles as described on pp. 22–23 of the aforementioned PCT application, including protonated, partially protonated and deprotonated forms thereof. Most preferably, the cationic amphiphile which is used to deliver the plasmids and/or viruses of the invention containing the components of the transgene expression system is spermine cholesterol carbamate (GL-67).

In the formulation of compositions comprising the transgene expression system of the invention, one or more cationic amphiphiles may be formulated with neutral co-lipids such as dileoylphosphatidylethanolamine (DOPE) to facilitate delivery of the transgene expression system into a cell. Other co-lipids which may be used in these complexes include, but are not limited to, diphytanoylphosphatidylethanolamine, lyso-phosphatidylethanolamines, other phosphatidylethanolamines, phosphatidylcholines, lyso-phosphatidylcholines and cholesterol. A preferred molar ratio of cationic amphiphile to colipid is 1:1. However, it is within the scope of the invention to vary this ratio, including also over a considerable range. In a preferred embodiment of the invention, the cationic amphiphile GL-67 and the neutral co-lipid DOPE are combined in a 1:2 molar ratio, respectively, before complexing with a plasmid and/or virus for delivery to a cell.

In one embodiment of the invention, where the transgene transcription unit is contained on a plasmid and the adenovirus E4 region is contained in an adenoviral vector, both plasmid and virus may be complexed with a cationic amphiphile for delivery to a cell. For example, the plasmid may be combined with GL-67:DOPE (1:2 molar ratio), and the adenovirus may be combined with 100% Gl-67, and equal volumes of each of these may be combined to form the plasmid/virus complex containing all components of the transgene expression system.

In the formulation of complexes containing a cationic amphiphile with a plasmid, a preferred range of from 0.4 mM–1 mM of cationic amphiphile may be combined with a range of 3 mM–8 mM of plasmid to form the complexes. In the formulation of complexes containing a cationic amphiphile with a virus, preferably adenovirus, a preferred range of $10^7$–$10^{10}$ infectious units of virus may be combined with a range of $10^4$–$10^6$ cationic amphiphile molecules/viral particle.

Assays may be performed in tissue culture systems to determine the persistence of expression of a transgene in vivo. Cell lines which may be transfected with the plasmids or infected with the viruses of the invention are suitable for assays which measure the level and duration of expression of a contained transgene. The transgene may encode a biologically useful protein or may encode a marker protein used to test persistence of the transgene expression system in vivo. Relevant molecular assays to determine the persistence of expression include the measurement of transgene mRNA, by, for example, Northern blot, S1 analysis or reverse transcription-polymerase chain reaction (RT-PCR). The presence of a protein encoded by a transgene may be detected by Western blot, immunoprecipitation, immunocytochemistry, or other techniques known to those skilled in the art.

In order to determine the persistence of transgene expression in vivo using the constructs and compositions of the invention, animal models are particularly relevant in order to assess transgene persistence against a background of potential host immune response. Such a model may be chosen with reference to such parameters as ease of delivery, identity of transgene, relevant molecular assays, and assessment of clinical status. Where the transgene encodes a protein whose lack is associated with a particular disease state, an animal model which is representative of the disease state may optimally be used in order to assess a specific phenotypic result and clinical improvement.

Relevant animals in which the transgene expression system may be assayed include, but are not limited to, mice, rats, monkeys, and rabbits. Suitable mouse strains in which the transgene expression system may be tested include, but are not limited to, C3H, C57B1/6 (wild-type and nude) and Balb/c (available from Taconic Farms, Germantown, N.Y.).

Where it is desirable to assess the host immune response to vector administration, testing in immune-competent and immune-deficient animals may be compared in order to define specific adverse responses generated by the immune system. The use of immune-deficient animals, e.g., nude mice, may be used to characterize vector performance and persistence of transgene expression, independent of an acquired host response, and to identify other determinants of transgene persistence.

In a particular embodiment where the transgene is the gene encoding cystic fibrosis transmembrane regulator protein (CFTR) which is administered to the respiratory epithelium of test animals, persistence of expression of CFTR may be assayed in the lungs of relevant animal models, for example, C57B1/6 or Balb/c mice, cotton rats, or Rhesus monkeys. Molecular markers which may used to determine the persistence of expression include the measurement of CFTR mRNA, by, for example, Northern blot, S1 analysis or RT-PCR. The presence of the CFTR protein may be detected by Western blot, immunoprecipitation, immunocytochemistry, or other techniques known to those skilled in the art. Such assays may also be used in tissue culture where cells deficient in a functional CFTR protein and into which the transgene expression system has been introduced may be assessed to determine the presence of functional chloride ion channels—indicative of the presence of a functional CFTR molecule.

The transgene expression system of the invention can be used to deliver and express any number of transgenes to cells in order to achieve a particular phenotypic result.

The present invention is further directed to compositions containing the transgene expression system of the invention which can be administered in an amount effective to deliver one or more desired transgenes to the cells of an individual in need of such molecules and cause persistent expression of a transgene encoding a biologically active protein to achieve a specific phenotypic result. The cationic amphiphile-plasmid complexes or cationic amphiphile-virus complexes may be formulated into compositions for administration to an individual in need of the delivery of the transgenes.

The compositions can include physiologically acceptable carriers, including any relevant solvents. As used herein, "physiologically acceptable carrier" includes any and all solvents, dispersion media, coatings, antibacterial and antifungal agents, isotonic and absorption delaying agents, and the like. Except insofar as any conventional media or agent is incompatible with the active ingredient, its use in the compositions is contemplated.

Routes of administration for the compositions containing the transgene expression system include conventional and physiologically acceptable routes such as direct delivery to the target organ or tissue, intranasal, intravenous, intramuscular, subcutaneous, intradermal, oral and other parenteral routes of administration.

The invention is further directed to methods for using the compositions of the invention in vivo or ex vivo applications in which it is desirable to deliver one or more transgenes into cells such that the transgene produces a normal biological or phenotypic effect. In vivo applications involve the direct administration of the transgene expression system formulated into a composition to the cells of an individual. Ex vivo applications involve the transfer of the transgene expression system directly to autologous cells which are maintained in vitro, followed by readministration of the transduced cells to a recipient.

Dosage of the transgene expression system to be administered to an individual for persistent expression of a transgene encoding a biologically active protein and to achieve a specific phenotypic result is determined with reference to various parameters, including the condition to be treated, the age, weight and clinical status of the individual, and the particular molecular defect requiring the provision of a biologically active protein. The dosage is preferably chosen so that administration causes a specific phenotypic result, as measured by molecular assays or clinical markers. For example, determination of the persistence of a transgene expression system containing the CFTR transgene which is administered to an individual can be performed by molecular assays including the measurement of CFTR mRNA, by, for example, Northern blot, S1 or RT-PCR analysis or the measurement of the CFTR protein as detected by Western blot, immunoprecipitation, immunocytochemistry, or other techniques known to those skilled in the art. Relevant clinical studies which could be used to assess phenotypic results from delivery of the CFTR transgene include PFT assessment of lung function and radiological evaluation of the lung. Demonstration of the delivery of a transgene encoding CFTR can also be demonstrated by detecting the presence of a functional chloride channel in cells of an individual with cystic fibrosis to whom the vector containing the transgene has been administered (Zabner et al., J. Clin. Invest. 97:1504–1511, 1996). The persistence of transgene expression in other disease states can be assayed analogously, using the specific clinical parameters most relevant to the condition.

Dosages of an adenoviral vector which contains all the components of the transgene expression system and which are effective to provide persistent expression of a transgene encoding a biologically active protein and achieve a specific phenotypic result range from approximately $10^8$ infectious units (I.U.) to $10^{11}$ I.U. for humans.

It is especially advantageous to formulate parenteral compositions in dosage unit form for ease of administration and uniformity of dosage. Dosage unit form as used herein refers to physically discrete units suited as unitary dosages for the subjects to be treated, each unit containing a predetermined quantity of active ingredient calculated to produce the specific phenotypic effect in association with the required physiologically acceptable carrier. The specification for the novel dosage unit forms of the invention are dictated by and directly depend on the unique characteristics of the transgene expression system and the limitations inherent in the art of compounding. The principal active ingredient (the transgene expression system) is compounded for convenient and effective administration in effective amounts with the physiologically acceptable carrier in dosage unit form as discussed above.

Maximum benefit and achievement of a specific phenotypic result from administration of the transgene expression system of the invention may require repeated administration. Where an adenoviral vector is used to deliver some or all of the components of the transgene expression system, such repeated administration may involve the use of the same adenoviral vector, or, alternatively, may involve the use of different vectors which are rotated in order to alter viral antigen expression and decrease host immune response.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See, e.g., *Current Protocols in Molecular Biology*, Ausubel et al., eds., John Wiley & Sons, Inc., New York, 1995, and *Remington's Pharmaceutical Sciences*, 17th ed., Mack Publishing Co., Easton, Pa., 1985.

The invention is further illustrated by the following specific examples which are not intended in any way to limit the scope of the invention.

EXAMPLE 1

CONSTRUCTION OF ADENOVIRAL VECTORS

Methods

Schematic diagrams of recombinant adenoviruses used in the experiments below illustrating specific transcription units and particular modifications to the adenovirus genome, including those to the E4 region, are depicted in FIG. 1.

The CMVβgal expression cassette was constructed in a pBR322-based plasmid that contained Ad2 nucleotides 1–10,680 from which nucleotides 357–3328 were deleted. The deleted sequences were replaced with a cytomegalovirus immediate early promoter (nucleotides −523 to −14, obtained from pRC/CMV, Invitrogen, Carlsbad, Calif.), lacZ gene encoding β-galactosidase with a nuclear localization signal (Kalderon et al., Cell 39:499–509, 1984) and an SV40 polyadenylation signal (nucleotides 2533–2729, Liebowitz et al., Curr. Top. Micro. Immunol. 87:43–172, 1979).

The E1aCFTR and E1aβgal expression cassettes were similarly constructed except the Ad2 deletion started from nucleotide 545. The cDNA for CFTR represents nucleotides 123–4622 of the published sequence and the lacZ gene was obtained as a NotI fragment from pCMVβ (Clontech, Palo Alto, Calif.).

The variations of the E4 region have been assigned a number, depending on the particular vector series. As shown in FIG. 1, for the CMV βgal, E1a CFTR, and E1Aβgal vector series, a wild type (wt) E4 region is assigned the number 1 and the Ad2E4ORF6 (Armentano et al., Human Gene Therapy 6:1343–1353, 1995, incorporated herein by reference) backbone is assigned the number 2. Variation number 3 (mORF6) is identical to 2 but includes an SV40 polyadenylation signal (nucleotides 2533–2729) inserted between the fiber region and ORF6. This modification corrects the reduced fiber synthesis that is observed with Ad2E4ORF6 (unpublished results). Variation number 4 (protein IX moved, PNM) is based on mORF6 and contains pIX sequences (nucleotides 3519–4061) that have been deleted and relocated between fiber and the SV40 polyadenylation signal. This modification helps to reduce the generation of replication competent adenovirus during virus expansion and has been invaluable for generating clinical grade preparations of virus (Hehir et al., J. Virol. 70:8459–8467, 1996). A complete E4 deletion, variation 5 (ΔE4), was constructed as follows. pAdORF6 (Armentano et al., Hum. Gene Ther. 6:1344–1353, 1995) was cut with BamHI and SalI which removes the ITR and E4ORF6. This was replaced with a BamHI-BglII fragment containing the SV40 polyadenylation signal and a BamHI-SalI fragnment generated by PCR containing Ad nucleotides 35642–35937 (E4 enhancer region and inverted terminal repeat).

Figure 2:
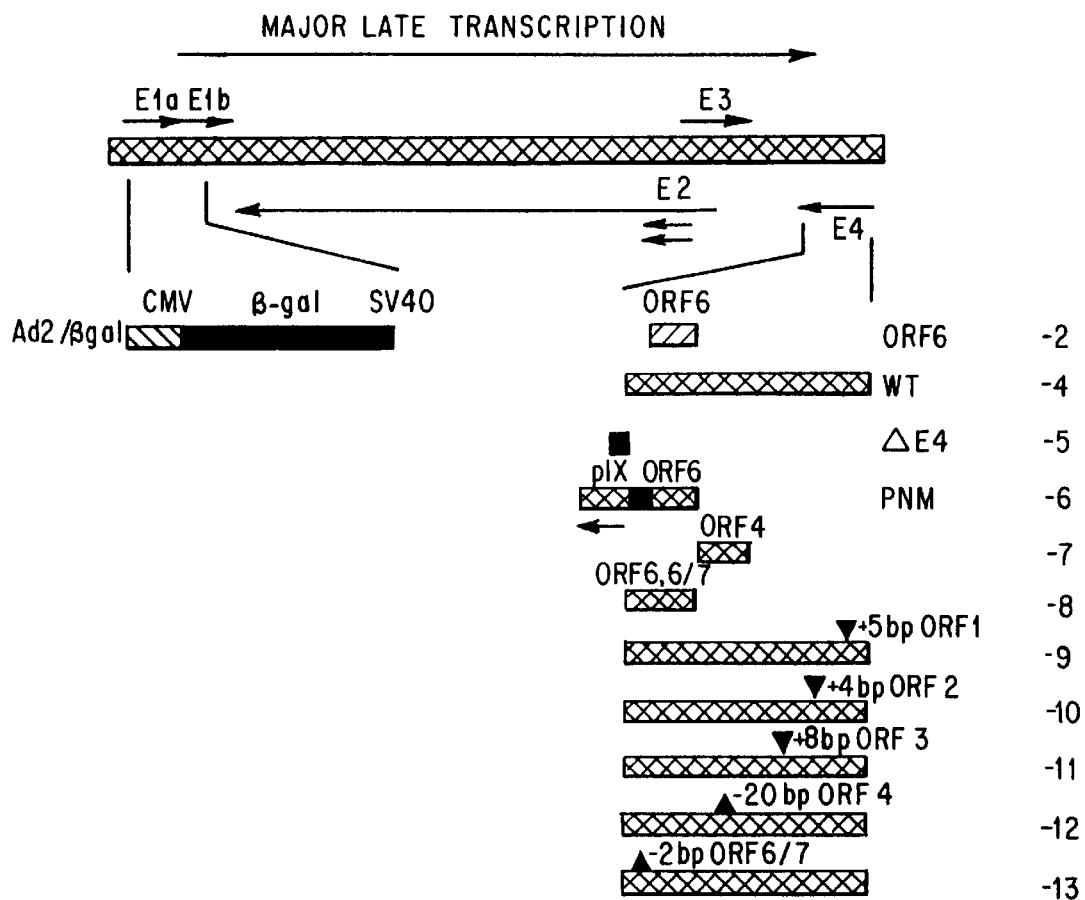
FIG. 2 shows a schematic diagram of the Ad2/βgal adenoviral vector series.

A schematic diagram of the Ad2/βgal vector series is shown in FIG. 2. Ad2/βgal-7 was made in VK2-20 cells by recombination of the large PacI fragment of Ad2/βgal-2 (corresponding to the left end of the virus) with the large PmeI fragment of dl366+ORF4 (corresponding to the right end). Ad2/βgal-8 through -13 were similarly made in 293 cells using Ad2/βgal-5 for recombination. Ad2/βgal-8 was made by recombination with E4dlORF1-4 which contains only ORFs 6 and 6/7 (Huang et al., J. Virol. 63:2605–2615, 1989). Viruses with knockouts of individual ORFs Ad2/βgal-9 (ORF1), Ad2/βgal-10 (ORF2), Ad2/βgal-11 (ORF3), Ad2/βgal-12 (ORF4) and Ad2/βgal-13 (ORF6/7) were derived from in 351, in 352, E4inORF3, dl358, and dl1356 respectively (Halbert et al., J. Virol. 56:250–257, 1985).

Some previously described vectors have been assigned a different name for simplicity. The vectors CMVβgal-1 and -2 refer to Ad2/βgal-2 and Ad2/βgal-4, respectively (Kaplan et al., Hum. Gene Ther. 8:45–56, 1997) and the vector E1aCFTR-4 (PNM) refers to Ad2/CFTR-8 (Hehir et al., J. Virol. 70:8459–8467, 1996).

All viruses, except those with complete E4 deletions, were propagated in 293 cells, purified and titered by end-point dilution using FITC conjugated anti-hexon antibody (Chemicon) as previously described (Armentano et al., Hum. Gene Ther. 6:1344–1353, 1995). Viruses with complete E4 deletions were propagated in VK2-20 cells, which is an E4 complementing cell line derived from 293 cells (Krougliak et al., Hum. Gene Ther. 6:1575–1586, 1995). Both 293 and VK2-20 cells were obtained from Dr. Frank Graham.

EXAMPLE 2

PERSISTENCE OF TRANSGENE EXPRESSION SYSTEM USING ADENOVIRUS E4 IN TRANS

Methods

Experiments were performed to test whether the effect of E4 could be supplied in trans from a vector that contains a wild type E4 region but does not contain a CMV promoter. For this purpose, nude mice were infected with CMVβgal-1 (wt E4) or CMVβgal-2 (ORF6) alone or were co-infected with E1aCFTR-1 (wt E4), E1aCFTR-4 (PNM) or E1aCFTR-5 (ΔE4). If a wild type E4 is required for persistence then co-infection of CMVβgal-1 (wt E4) with any of the E1aCFTR series should not alter the expression profile and persistence of expression should be observed in all cases. If E4 is required but its effect can be supplied in trans then co-infection of CMVβgal-2 (ORF6) with E1aCFTR-1 (wt E4) should result in persistence of expression similar to that which is observed with CMVβgal-1 (wt E4). In contrast, co-infection with either E1aCFTR-4 (PNM) or -5 (ΔE4) should not effect expression and an expression profile similar to that observed in animals that received CMVβgal-2 alone would be expected.

Balb/c parental and nude mice were purchased from Taconic Farms (Germantown, N.Y.). Animals, mostly females, ranging from 7 to 16 weeks old were used for in vivo studies. Mice were anesthetized by inhalation of Metofane (methoxyflurane) and were instilled intranasally with recombinant virus in 100 μl PBS, 3% sucrose.

Mice were intranasally instilled with $1.5 \times 10^9$ I.U. of CMVβgal-1 (A-D) or CMVβgal-2 (E-H) alone (A, E) or along with $1.5 \times 10^9$ I.U. E1aCFTR-1 (B, F), $1.5 \times 10^9$ I.U. E1aCFTR-4 (C, G) or $4.3 \times 10^8$ I.U. E1aCFTR-5 (D, H). Mice were sacrificed on days 3 and 14, lungs from individual animals were homogenized, and β-galactosidase activity was measured by an AMPGD (3-(4-methoxyspiro [1,2-dioxethane-3,2'-tricyclo-[$3.3.1.1^{3,7}$] decan]-4-yl) phenyl-β-D-galactopyranoside)(Galactolight™) assay (Tropix, Bedford, Mass.). The protein concentration in lung homogenates was measured with the BioRad (Hercules, Calif.) DC reagent and β-galactosidase activity is expressed as relative light units (RLU/μg protein). Each bar represents the average activity from at least three animals.

Results

Figure 3:
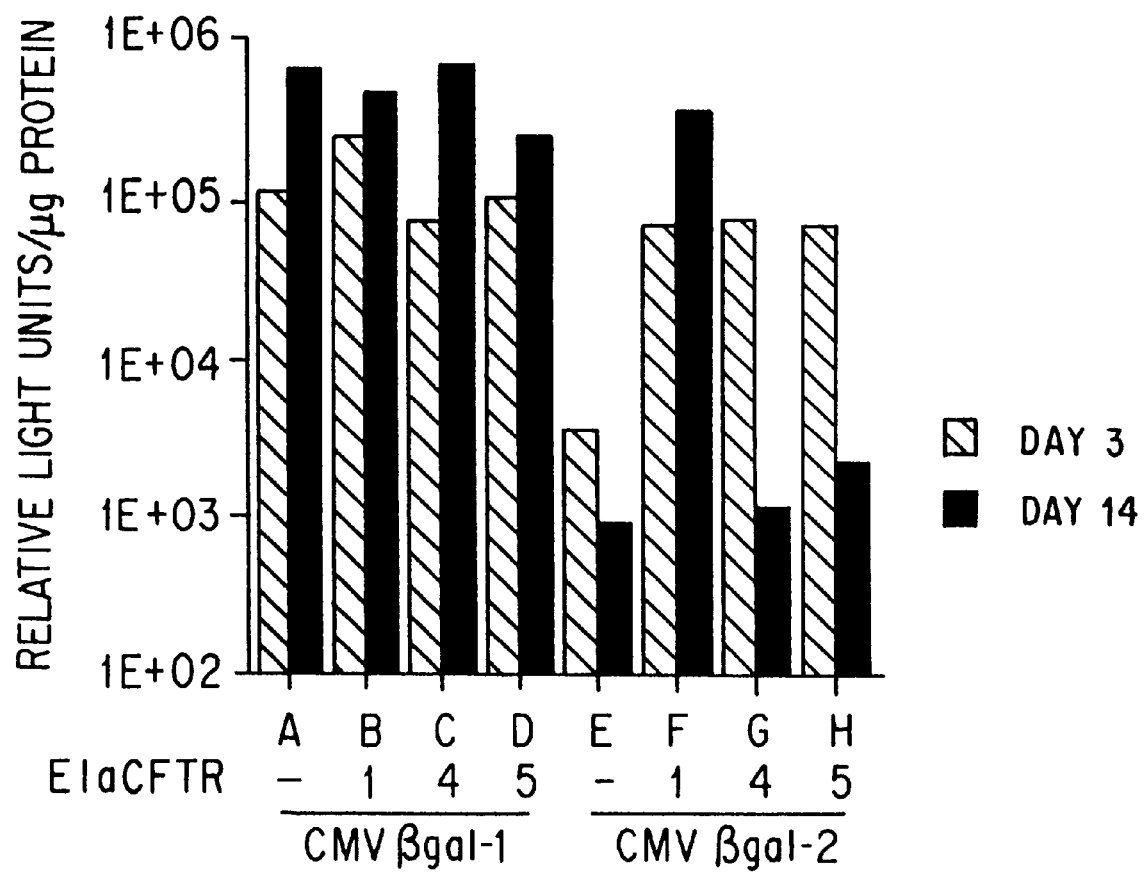
FIG. 3 shows the effect of adenovirus E4 on β-galactosidase expression in nude mice.

The results shown in FIG. 3 indicate that the expression profile from CMVβgal-1 (A) remains unchanged in animals that were co-infected with any of the E1aCFTR vectors (B, C and D). Expression from CMVβgal-2 (E) drops by day 14 in animals that were co-infected with E1aCFTR-4 or -5 (G,H). However, expression on day 14 in animals that were co-infected with E1aCFTR-1(F) remains elevated and is similar to that seen in animals that received CMVβgal-1 (A-D). This suggests that an E4 product(s) is supplied in trans and can act, either directly or indirectly, to allow persistence of expression from the CMV promoter.

EXAMPLE 3

PERSISTENCE OF TRANSGENE EXPRESSION SYSTEM IN TISSUE CULTURE

Methods

A co-infection study was performed in cultured rat hepatocytes to determine if an E4 requirement for expression from the CMV promoter would be observed in tissues other than the lung, and if the E4 function could be provided in trans. Primary rat hepatocytes were infected with CMVβgal-1 or -2 alone at an MOI (multiplicity of infection) of 10 or were co-infected at an MOI of 10 with E1aCFTR-1, -4 or -5 and were analyzed for β-galactosidase expression by X-gal staining.

Results

Figures 4A, 4B:
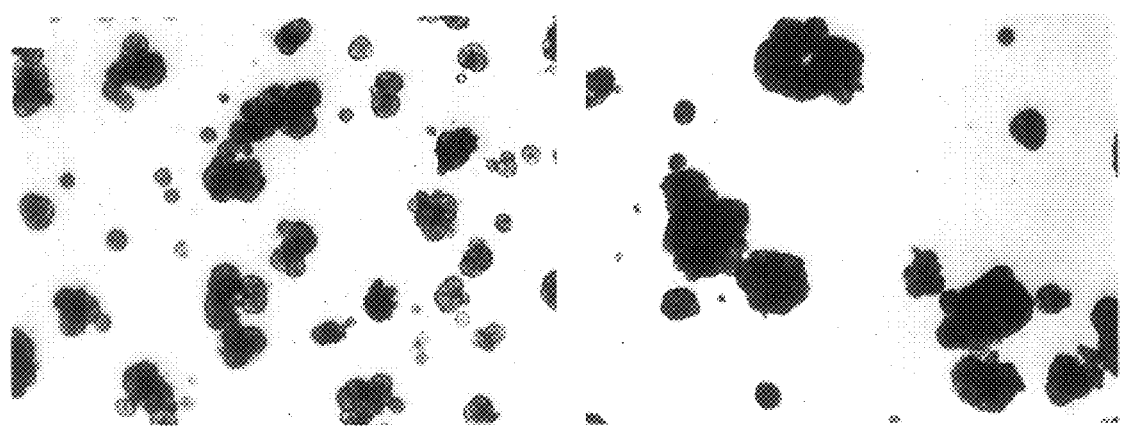
FIGS. 4(A–F) shows the effect of adenovirus E4 on β-galactosidase expression in rat hepatocytes.
Figures 4C, 4D:
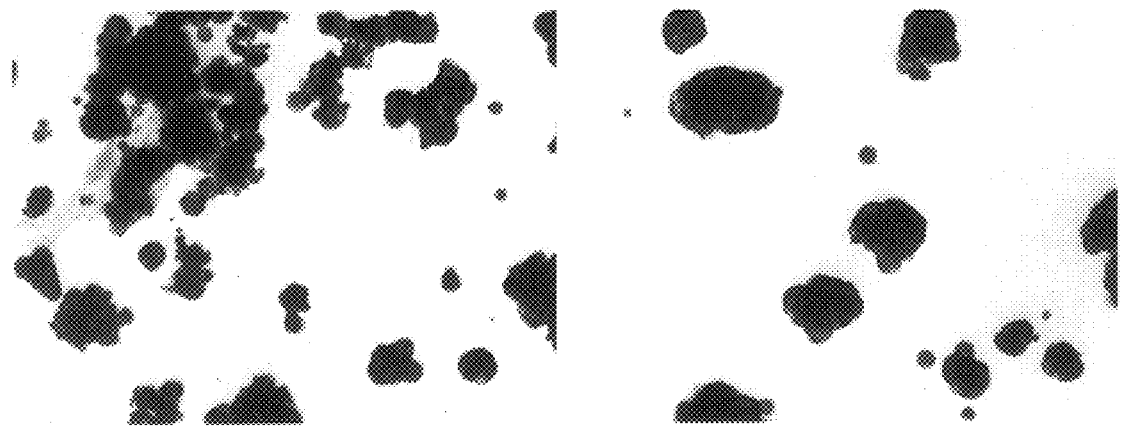
Figures 4E, 4F:
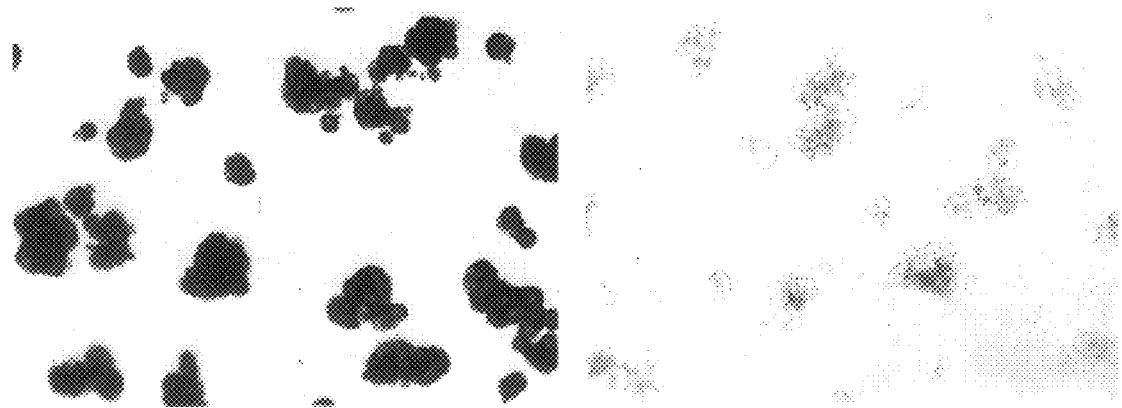
Figure 5A:
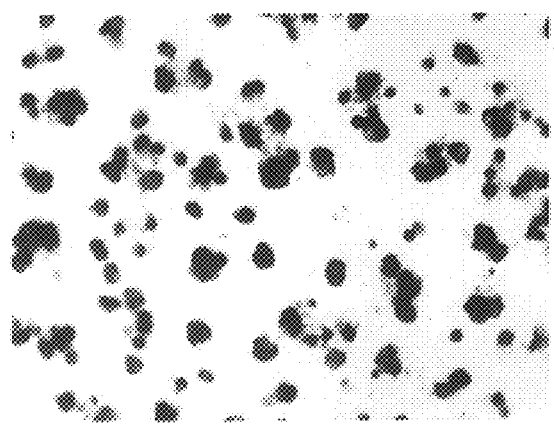
FIGS. 5(A–F) shows the effect of adenovirus E4 on β-galactosidase expression in rat hepatocytes.
Figure 5B:
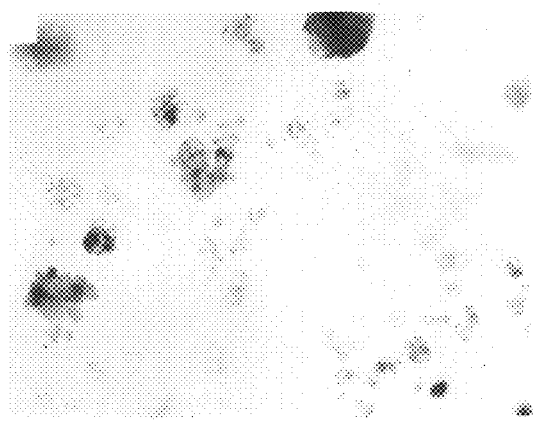
Figure 5C:
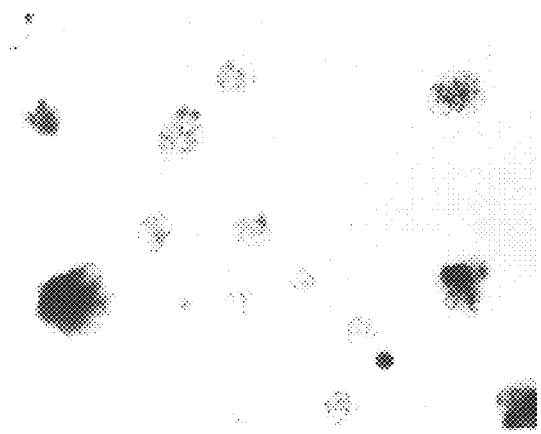
Figure 5D:
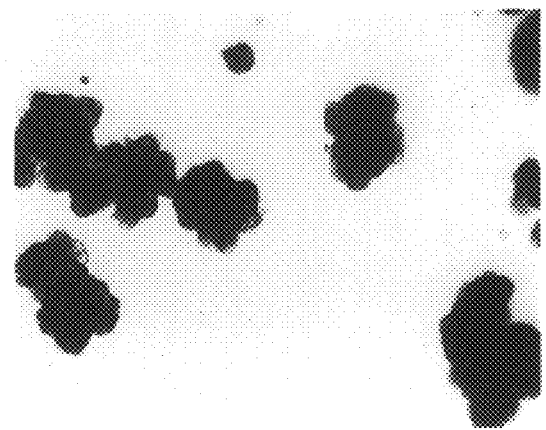
Figure 5E:
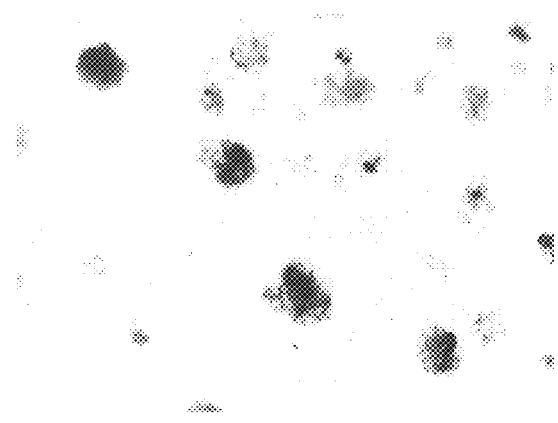
Figure 5F:
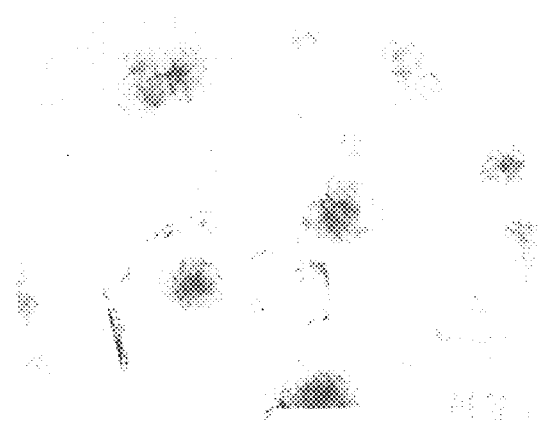

FIG. 4, panel A and B, depict β-galactosidase expression observed with CMVβgal-1 on days 3 and 14 post-infection, respectively. Panels C, D and E correspond to expression observed 14 days post-infection in cultures that were co-infected with E1aCFTR-4, -1 and -5, respectively. In all cases, expression seems to persist to day 14.

Panels A and B in FIG. 5 represent CMVβgal-2 infected cultures analyzed on days 3 and 14 post-infection, respectively. Expression with this vector in hepatocytes has clearly diminished during this time period. Co-infection with E1aCFTR4, -1 and -5, shown in panels C, D and E indicates that expression declines by day 14 except in the culture that was co-infected with E1aCFTR-1. These results demonstrate a requirement for E4 for prolonged expression from the CMV promoter in cultured hepatocytes as well as was the case in the mouse lung, and that the E4 function required for persistent expression can be provided in trans.

EXAMPLE 4

EFFECT OF SPECIFIC E4 OPEN READING FRAMES ON THE PERSISTENCE OF EXPRESSION IN THE MOUSE LUNG

Methods

Experiments were performed to determine whether specific open reading frames of the adenovirus E4 region were required for persistent expression of a transgene from the CMV promoter. Recombinant adenoviral vectors in which particular open reading frames of the E4 region were retained or deleted were used in the experiments.

Balb/c nude mice were intranasally instilled with $3 \times 10^9$ infectious units of Ad2/βgal-4 (wild-type E4), Ad2/βgal-7 (containing ORF4), or Ad2/βgal-8 (containing ORF6 and ORF6/7)(FIG. 2). Mice were sacrificed on days 3 and 14 and β-galactosidase activity in the lungs of the test animals was determined as described in Example 2, infra. Each time point represents the average from four animals.

Results

Figure 6:
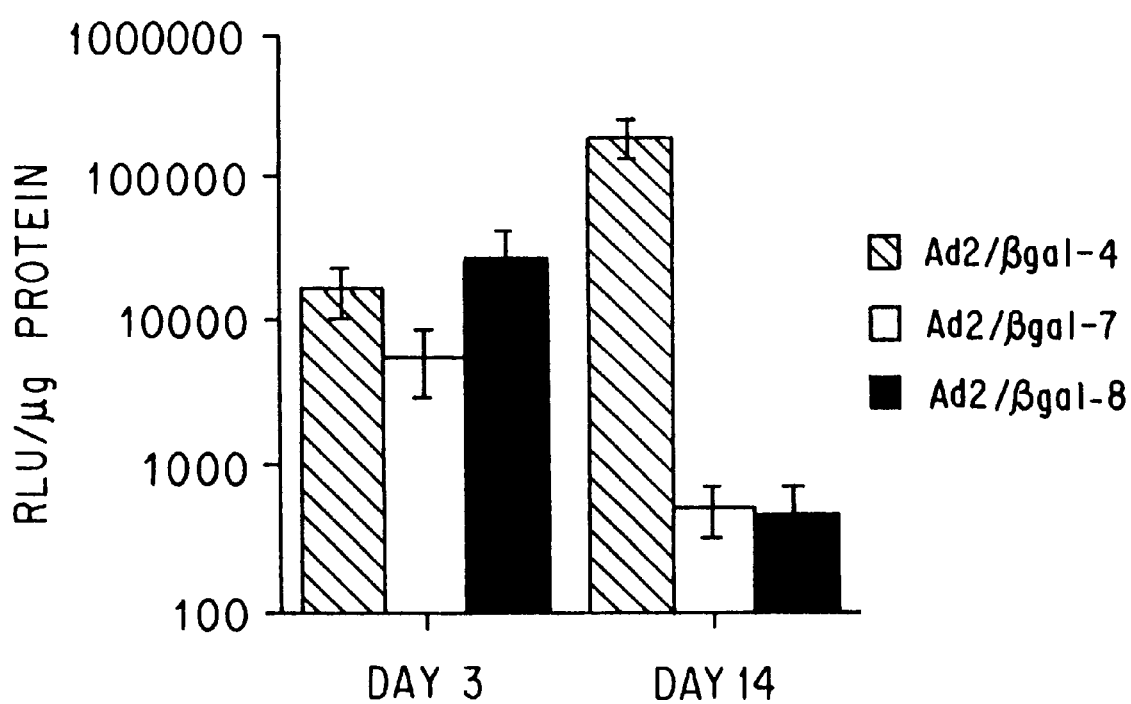
FIG. 6 shows the expression of β-galactosidase using E4-modified adenoviral vectors in nude mice.

FIG. 6 shows that expression persisted to day 14 in animals that received Ad2/βgal-4, containing wild-type E4. Expression declined from day 3 to day 14 in animals that received Ad2/βgal-7 or Ad2/βgal-8. This suggests that neither ORF4 nor ORFs 6 and 6/7 are sufficient to achieve longevity of expression from the CMV promoter.

EXAMPLE 5

EFFECT OF SPECIFIC E4 OPEN READING FRAMES ON THE PERSISTENCE OF EXPRESSION IN RAT HEPATOCYTES

Methods

Rat hepatocytes were infected with viruses in the Ad2/βgal series (FIG. 2) at a MOI of 10. B-galactosidase expression was visualized by X-gal staining of the infected hepatocytes on days 3 and 14 post-infection.

Results

Figure 7A:
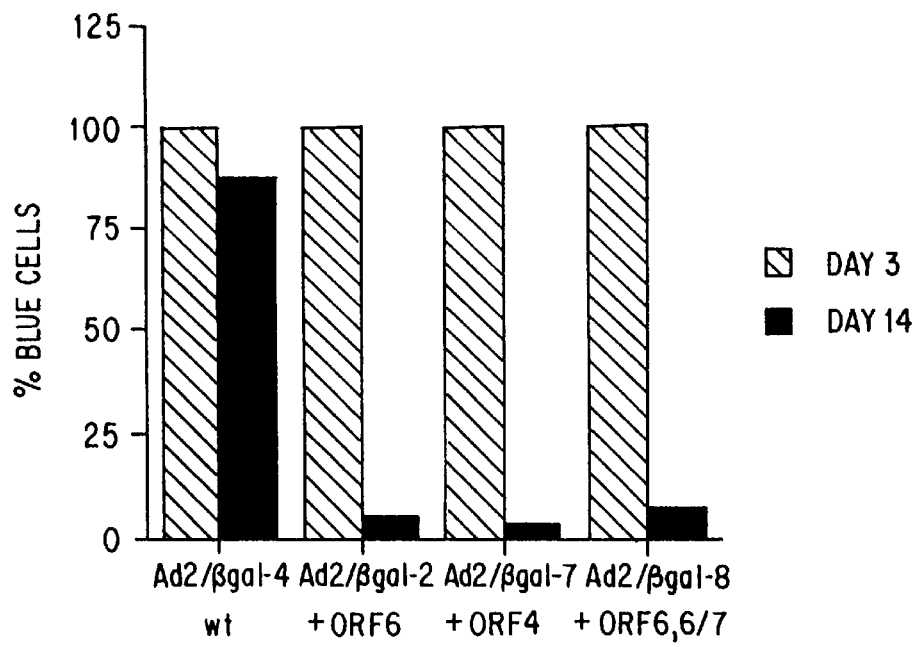
FIG. 7A shows the expression of β-galactosidase from E4-modified adenoviral vectors in rat hepatocytes.

The graph in FIG. 7A represents the percentage of stained cells in the cells infected with adenoviral vectors containing specific E4 open reading frames: Ad2/βgal-2, Ad2/βgal-7, and Ad2/βgal-8 (FIG. 2). As previously observed, expression persists in rat hepatocytes with a vector that contains a wild-type E4 region (Ad2/βgal-4), but does not persist with a vector containing only ORF6 (Ad2/βgal-2). As shown here in the upper panel, expression does not persist in hepatocytes that were infected with either a vector containing only ORF 4 (Ad2/βgal-7) or a vector containing only ORFs 6 and 6/7 (Ad2/βgal-8). The data suggest that ORF4 or ORFs 6 and 6/7 are not sufficient to allow persistent expression from the CMV promoter.

Figure 7B:
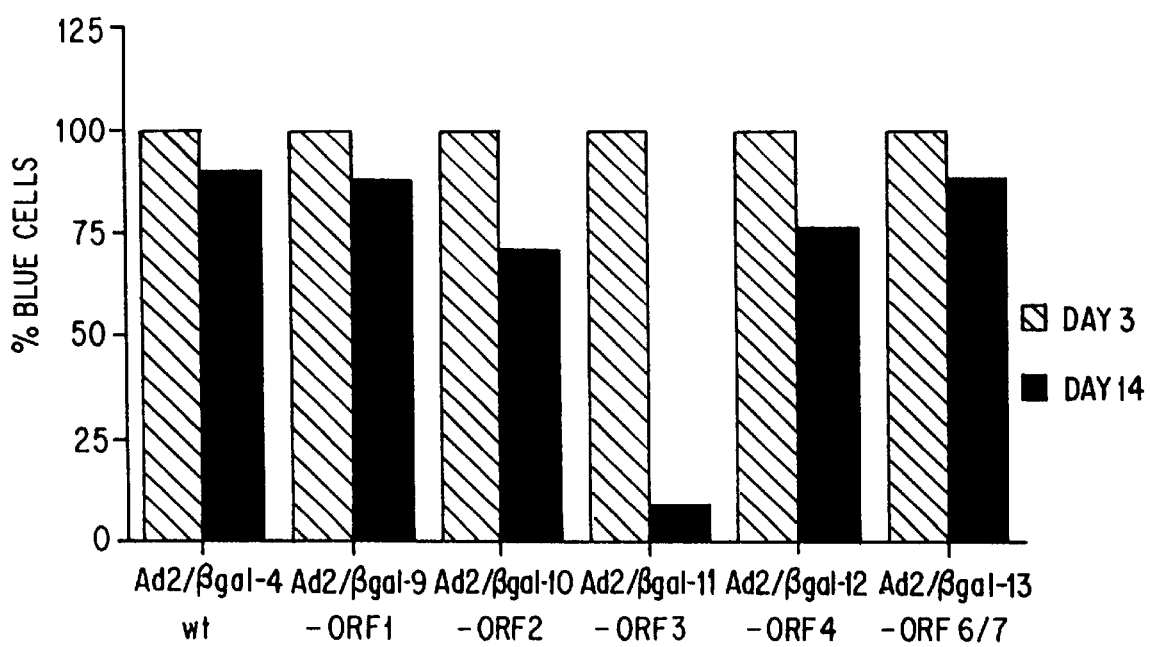
FIG. 7B shows expression using adenoviral vectors deleted for specific E4 open reading frames.

The graph in FIG. 7B represents results obtained in rat hepatocytes infected with adenoviral vectors containing knockouts of individual E4 ORFs (Ad2/βgal-9 through Ad2/βgal-13, FIG. 2). Expression persists in all cultures infected with viruses containing individual ORF knockouts except the culture that was infected with the ORF3 knockout (Ad2/βgal-11). The data suggest that ORFs 1, 2, 4, and 6/7 are not required to achieve long-term expression and implicate ORF3 as playing a role in the observed effect of E4 on persistent expression from the CMV promoter. The data indicate that ORF3 is, at least, required to achieve persistence of expression from the CMV promoter.

EXAMPLE 6

PERSISTENCE OF HYBRID PLASMID/VIRUS TRANSGENE EXPRESSION SYSTEM IN MICE

Figure 8:
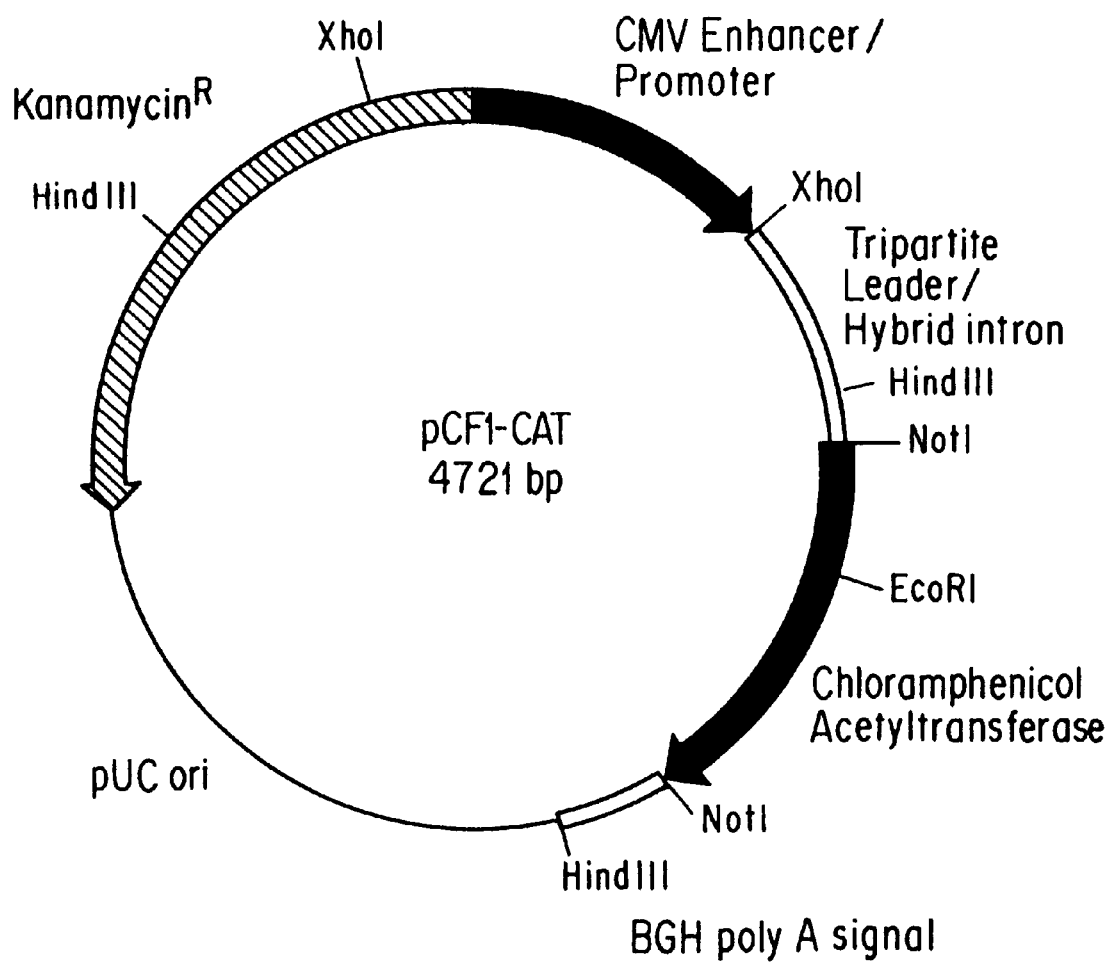
FIG. 8 shows a schematic diagram of plasmid pCF1-CAT.

To create plasmid pCF1-CAT (FIG. 8), the vector pCMVβ (Clontech, Palo Alto, Calif.) was first digested with NotI to excise the β-galactosidase gene to form pCMV containing the CMV immnediate early promoter from −522 to +72 (Boshart et al., Cell 41:521–530, 1985). The bovine growth hormone (BGH) poly A signal was amnplified from the vector pcDNA3 (Invitrogen, San Diego, Calif.) using the polymerase chain reaction (PCR). The 241 bp PCR product was subcloned into the vector PCR-U (Invitrogen, San Diego) to form pCRII-BGH. The NotI-HindIII BGH fragmnent was excised and ligated into the NotI and HindIII sites of pCMV, replacing the SV40 poly A signal, to form pCMV-BGH. The hybrid intron was obtained from the vector pADB (Clontech, Palo Alto, Calif.). pADB was digested with PmlI and NotI, and the −500 bp fragment was isolated then ligated into the HincII and NotI sites of pBluescript11 KS(−) (Stratagene, La Jolla, Calif.) to form pBlueII-HI2. pBlueII-HI2 was digested with XhoI and NotI to excise the hybrid intron fragnment. This fragment was ligated into the XhoI and NotI sites of pCMV-BGH, replacing the SV40 intron to form pCMVHI2BGH. The aminoglycoside 3'phosphotransferase (APT) gene, which confers resistance to kanamycin, was obtained from the vector pUC4K (Pharmacia, Piscataway, N.J.). pUC4K was digested with EcoRI to excise the 1.3 kb APT gene. The EcoRI ends were blunted using the Klenow fragment of DNA polymerase I. pCMV was digested with AlwNI and EcoRI and the ends blunted with Klenow. The APT fragment was ligated into the pCMV vector, replacing the ampicillin resistance gene to form pCMV/kan. pCMV/kan was digested with NcoI and AlwNI to excise the APT gene and flanking sequences. This fragment was ligated into the NcoI and AlwNI sites of pCMVHI2BGH to form pCMVM2BGH/kan. The chloramphenicol acetyltransferase (CAT) cDNA was obtained from the CAT Geneblock (Pharmacia), and NotI linkers were added to the ends of the cDNA. pCMVHI2BGH/kan was digested with NotI and ligated to the CAT cDNA to form pCF1-CAT (FIG. 8).

The p5GΔCECMV-CAT (p5GminCMV-CAT) plasmid was derived from pCFI-CAT. A small polylinker was inserted 5' to the CMV enhancer/promoter of pCMVHI2BGH/kan (see above) to form pCMV(A-N)kan. Five yeast GAL4 binding sites were assembled from four synthetic oligonucleotides and inserted into the polylinker AvrII site of pCMV(A-N)kan. A 322 bp AatII fragment (deleting the CMV enhancer from −462 to −141 relative to the transcription start site) was removed, then the CAT cDNA was ligated into the NotI site to form p5GΔCE-CAT (p5GminCMV-CAT).

Cationic amphiphile-plasmid complexes were formed between GL67-DOPE (1:2) with pCF1-CAT (0.6:3.6 mM) and GL-67 (100%) with adenovirus (Ad2/CMVβgal-4, containing wild type E4 or Ad2/CMVβgal-5, lacking E4) (approximately $3 \times 10^5$ GL-67 molecules/virus particle and about $10^9$ infectious units/mouse). The lipid-DNA and lipid-virus complexes were formed by warming all components for 5 minutes to 30° C., adding lipid to DNA or to virus with no agitation (140 μl of lipid was added to 140 μl of either DNA or virus), and allowing complexes to stand at 30° for 15 minutes. The two complexes were combined.

The mixture of both complexes was instilled intranasally into nude Balb/c mice in two doses of 50 μl each. The animals were sacrificed at the time points indicated. Extracts from the lungs of the mice installed with the complexes were evaluated for β-gal activity generated from the adenovirus (positive control) and for CAT activity generated from the plasmid.

Lungs from individual animals were homogenized and β-galactosidase activity was assayed as described in Example 2, infra. CAT activity was detected by a standard isotopic assay (see, e.g., short protocols in Molecular Biology, 3rd ed., Ausubel et al., eds., Wiley and Sons, New York, 1995).

Results

Figure 9:
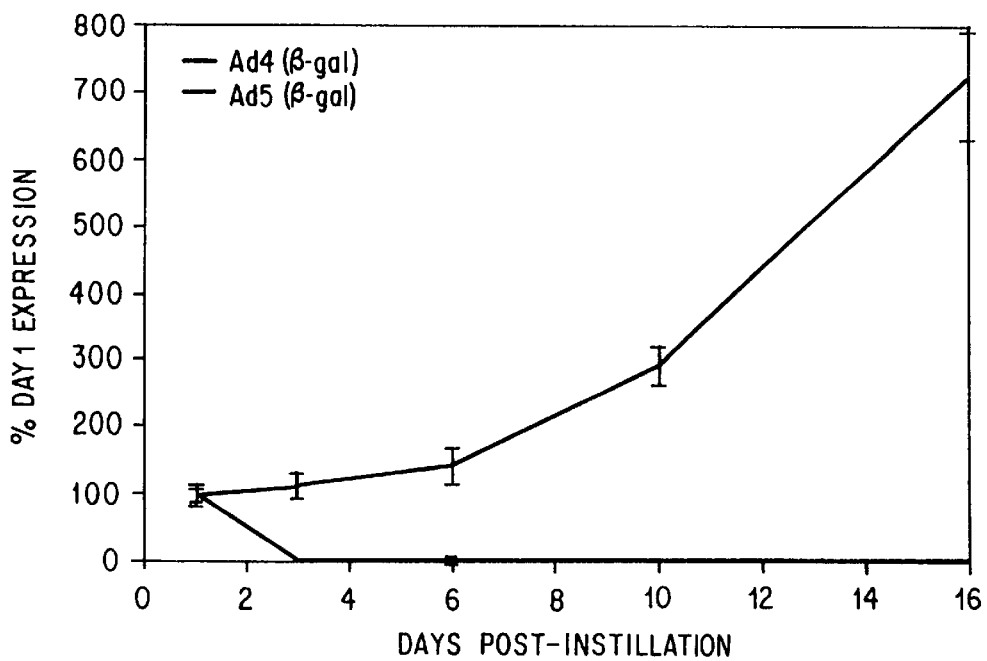
FIG. 9 shows the persistence of expression of β-galactosidase from an adenoviral vector in nude mice.
Figure 10:
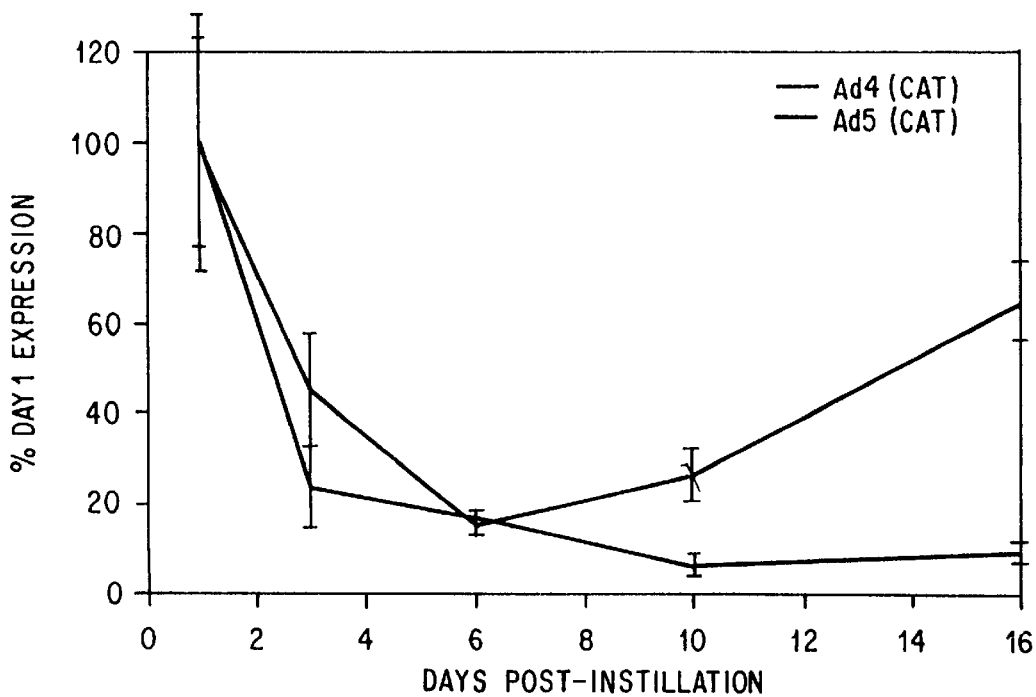
FIG. 10 shows the persistence of expression of CAT from pCF1-CAT in nude mice at 16 days.
Figure 11:
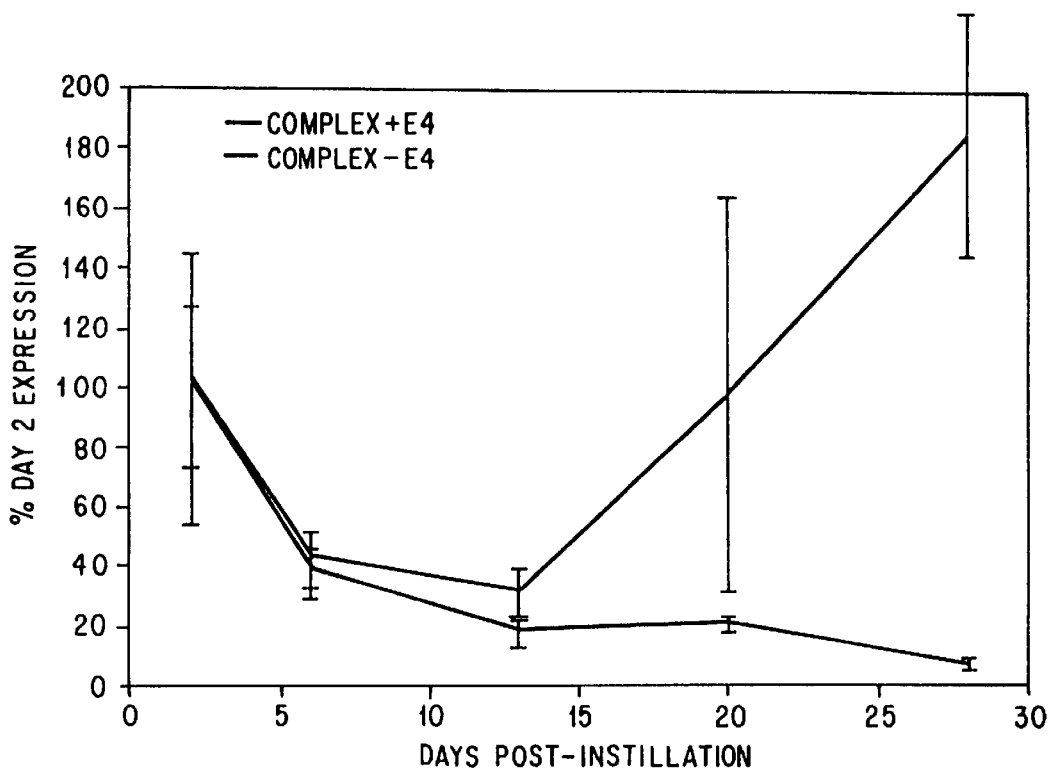
FIG. 11 shows the persistence of expression of CAT from pCF1-CAT in nude mice at 28 days.

The experiments were performed to determine if expression of the transgene could be achieved using a plasmid containing the transcription unit with a CMV promoter and an adenovirus containing the E4 region which were simultaneously introduced to the cell by cationic amphiphile-mediated delivery. The assays were performed at various times post-installation and the results are shown in FIGS. 9, 10, and 11. Transgene expression is shown as a function of the initial level of expression.

In FIG. 9, the β-gal expression from the adenovirus demonstrated that the vector containing wild-type E4 (Ad2/CMVβgal-4) showed persistence of expression over 16 days, with increasing levels of β-gal detectable over time. The vector deleted for E4 (Ad2/CMVβgal-5) showed a rapid loss of β-gal expression (starting off from an absolute level about 50% of that from the Ad2/CMVβgal-4 vector).

FIG. 10 shows that the CAT activity from the plasmid vectors showed similar trends when instilled +/− wild-type E4 up to 6 days. The expression of CAT in the E4-deleted mice continued to decline over 16 days whereas the E4+ mice showed a steady increase up to about 70% of day 1 levels of expression (FIG. 10). When CAT expression from pCF1-CAT was determined over a 28-day period, the presence of the adenovirus E4 region supplied by Ad2/βgal-4 correlated with significantly higher expression at day 28 than that detected in its absence (FIG. 11). The results demonstrate the necessity of the E4 region for persistence of the plasmid-derived reporter gene expression.

EXAMPLE 7

EFFECT OF PROMOTER TRUNCATIONS ON THE PERSISTENCE OF EXPRESSION FROM THE CMV PROMOTER

Methods

An experiment was performed to determine if the full length CMV promoter was required for persistent expression by the transgene expression system. Plasmids pCF1-CAT and p5GminCMV-CAT were introduced into nude Balb/c mice as described in Example 6, infra., together with the adenovirus E4 region supplied by Ad2/βgal-4, and expression was monitored for 14 days post-instillation.

Results

Figure 12:
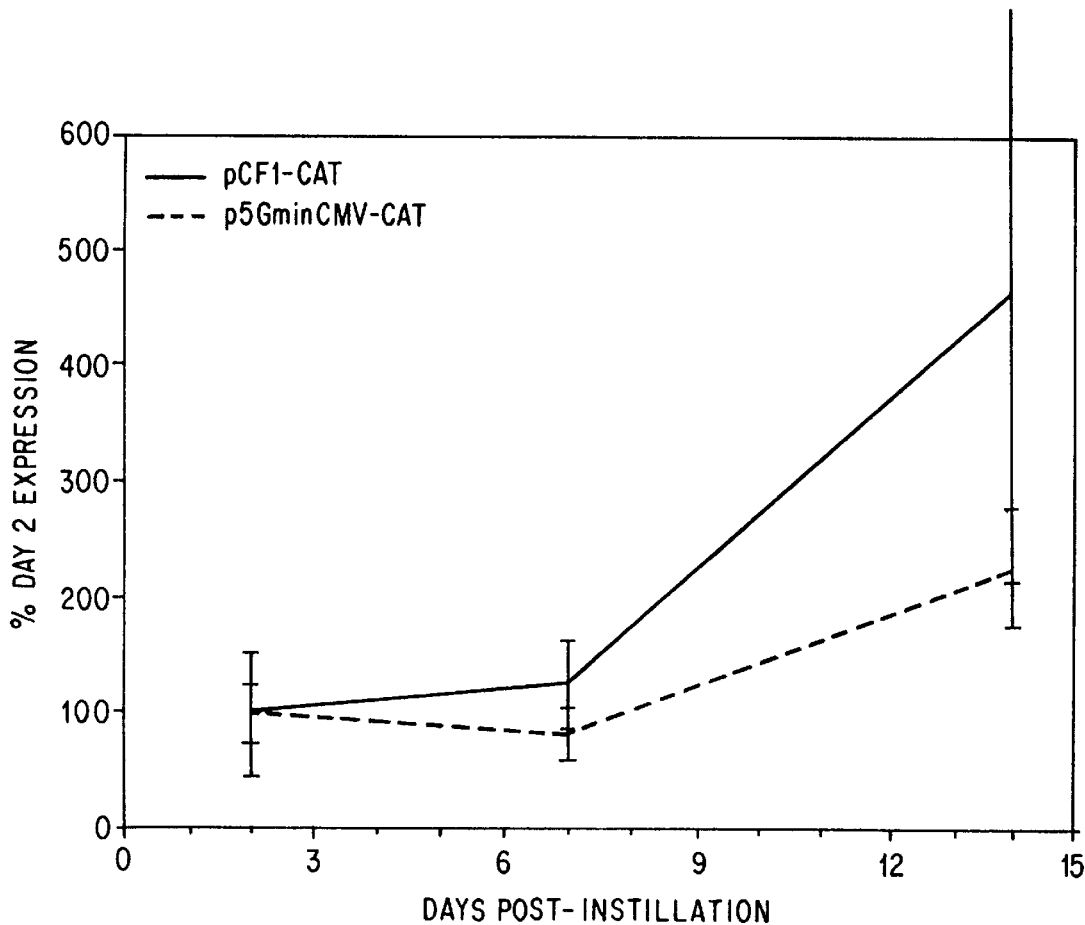
FIG. 12 shows the persistence of expression of CAT expressed from a wild-type or truncated CMV promoter in nude mice.

FIG. 12 shows that persistence of CAT expression over 14 days is maintained in nude mice using the full pCF1-CAT promoter region or a plasmid containing a large deletion of part of the CMV promoter sequence (p5GminCMV-CAT).

We claim:

1. A plasmid comprising a transgene expression system, said system comprising;
   a) a transgene operably linked to an expression control sequence, and
   b) one or more adenovirus E4 open reading frames (ORF).

2. The plasmid of claim 1 wherein the expression control sequence comprises a cytomegalovirus promoter.

3. The plasmid of claim 1 wherein the transgene expression system comprises an adenovirus E4 ORF3.

4. The plasmid of claim 3 wherein the expression control sequence comprises a cytomegalovirus promoter.

* * * * *